(12) United States Patent
Bassell et al.

(10) Patent No.: US 9,458,458 B2
(45) Date of Patent: Oct. 4, 2016

(54) MANIPULATING MICRORNA FOR THE MANAGEMENT OF NEUROLOGICAL DISEASES OR CONDITIONS AND COMPOSITIONS RELATED THERETO

(71) Applicant: EMORY UNIVERSITY, Atlanta, GA (US)

(72) Inventors: Gary J. Bassell, Snellville, GA (US); Xiaodi Yao, Decatur, GA (US); Christina Gross, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/474,965

(22) Filed: Sep. 2, 2014

(65) Prior Publication Data

US 2015/0133522 A1    May 14, 2015

Related U.S. Application Data

(60) Provisional application No. 61/902,337, filed on Nov. 11, 2013.

(51) Int. Cl.
*A61K 48/00* (2006.01)
*C12N 15/113* (2010.01)

(52) U.S. Cl.
CPC ....... *C12N 15/113* (2013.01); *C12N 2310/113* (2013.01); *C12N 2310/315* (2013.01); *C12N 2310/3231* (2013.01)

(58) Field of Classification Search
None
See application file for complete search history.

(56) References Cited

U.S. PATENT DOCUMENTS

| 8,116,987 B2 | 2/2012 | Delfour | |
|---|---|---|---|
| 2010/0004320 A1* | 1/2010 | Elmen et al. | 514/44 R |
| 2010/0204309 A1 | 8/2010 | Herbert | |

FOREIGN PATENT DOCUMENTS

| WO | 2008/074328 | 6/2008 |
|---|---|---|
| WO | 2011/079299 | 6/2011 |

OTHER PUBLICATIONS

Gross et al. "Fragile X Mental Retardation Protein Regulates Protein Expression and mRNA Translation of the Potassium Channel Kv4.2" The Journal of Neuroscience, 2011; 31(15): 5693-5698.

Gross et al. "Therapeutic Strategies in Fragile X Syndrome: From Bench to Bedside and Back" Neurotherapeutics, 2015; 12(3): 584-608.

Gross et al. "Selective role of the catalytic PI3K subunit p110β in impaired higher order cognition in fragile X syndrome" Cell Rep., 2015; 11(5): 681-688.

Hall et al. "Tau and potassium channel Kv4.2 in Alzheimer disease-related neuronal dysfunction" Program No. 352.02/V7, 2011 Neuroscience Meeting Planner, Washington, DC: Society for Neuroscience, 2011. Online.

Jimenez-Mateos et al. "Silencing microRNA-134 produces neuroprotective and prolonged seizure-suppressive effects" Nat Med., 2012; 18(7): 1087-1094.

Jimenez-Mateos et al. "Epilepsy and microRNA" Neuroscience, 2013; 238: 218-229.

Kim et al. "Identification of many microRNAs that copurify with polyribosomes in mammalian neurons" Proc Natl Acad Sci U S A., 2004; 101(1): 360-365.

Lee et al. "Bidirectional Regulation of Dendritic Voltage-Gated Potassium Channels by the Fragile X Mental Retardation Protein" Neuron, 2011; 72(6): 1091.

Levisohn "The autism-epilepsy connection" Epilepsia, 2007; 48(Suppl. 9): 33-35.

Matkovich et al. "MicroRNA-133a Protects Against Myocardial Fibrosis and Modulates Electrical Repolarization Nithout Affecting Hypertrophy in Pressure-Overloaded Adult Hearts" Circ Res., 2010;106(1): 166-175.

Noebels "A Perfect Storm: Converging Paths of Epilepsy and Alzheimer's Dementia Intersect in the Hippocampal Formation" Epilepsia, 2011; 52(Suppl 1): 39-46.

Richter et al. "Dysregulation and restoration of translational homeostasis in fragile X syndrome" Nat Rev Neurosci., Oct. 2015; 16(10): 595-605.

Singh et al. "A Kv42 truncation mutation in a patient with temporal lobe epilepsy" Neurobiology of Disease, 2006; 24: 245-253.

\* cited by examiner

*Primary Examiner* — Kimberly Chong
(74) *Attorney, Agent, or Firm* — Emory Patent Group

(57) ABSTRACT

This disclosure relates to manipulating microRNA for the management of neurological disorders and compositions related thereto. In certain embodiments, the disclosure contemplates inhibition of miR324 or miR324-5p, e.g., the use of nucleobase polymers for antisense disruptions or RNA interference of miR-324 expression or for miR324-5p binding in order to increase Kv4.2 expression. In certain embodiments, the disclosure relates to methods of treating or preventing a neurological disease or condition comprising administering an effective amount of an inhibitor to a subject in need thereto.

3 Claims, 5 Drawing Sheets

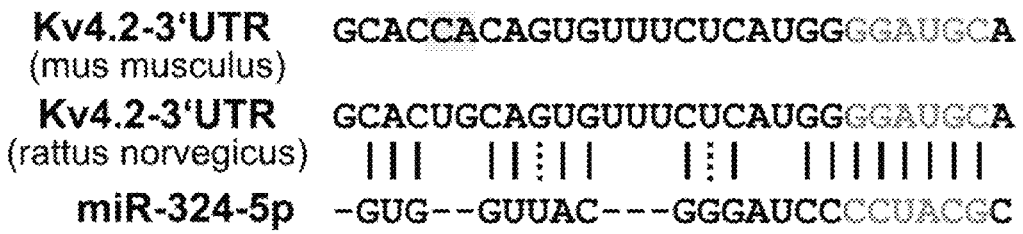
FIG. 2A
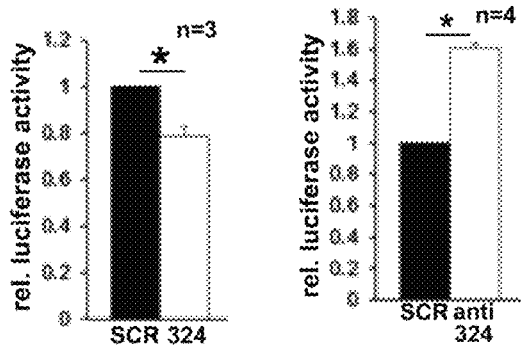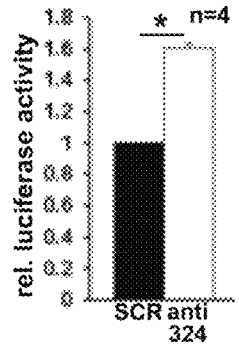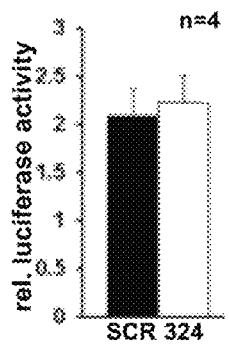
FIG. 2B　　FIG. 2C　　FIG. 2D
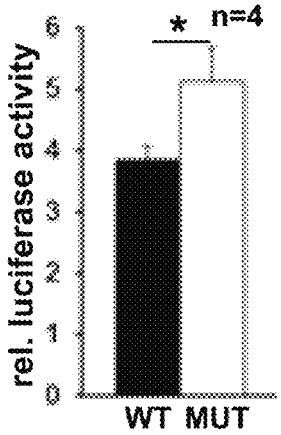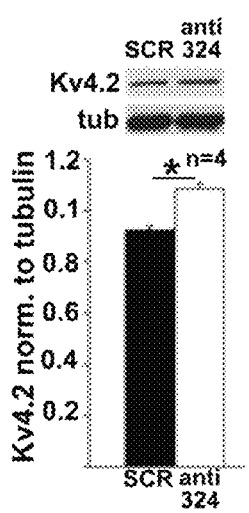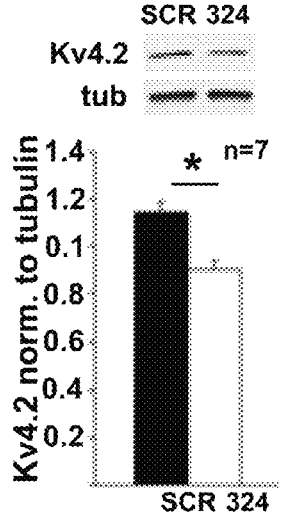
FIG. 2E　　FIG. 2F　　FIG. 2G

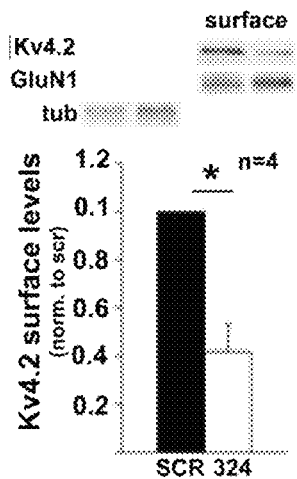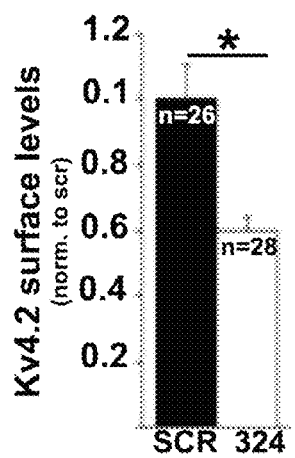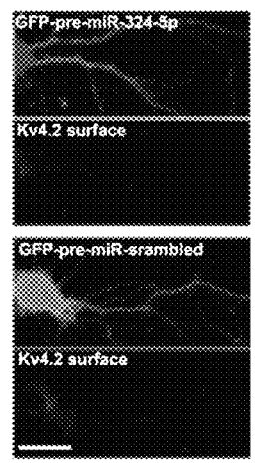
FIG. 2H  FIG. 2I  FIG. 2J
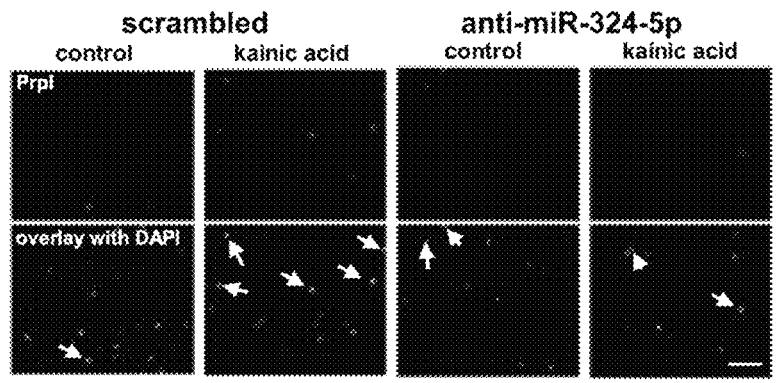
FIG. 3A
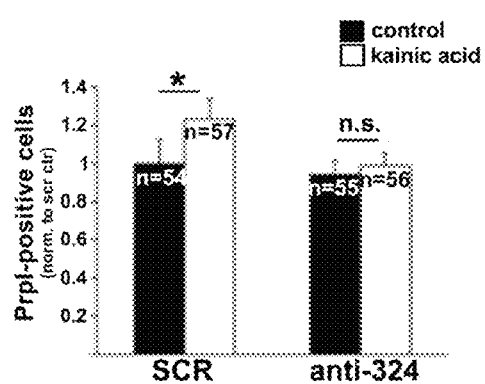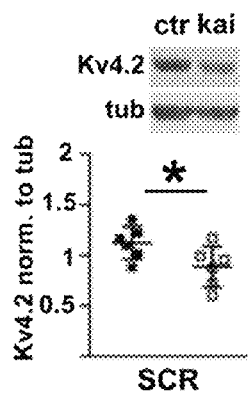
FIG. 3B  FIG. 3C

MANIPULATING MICRORNA FOR THE MANAGEMENT OF NEUROLOGICAL DISEASES OR CONDITIONS AND COMPOSITIONS RELATED THERETO

CROSS-REFERENCE TO RELATED APPLICATIONS

This application claims priority to U.S. Provisional Application No. 61/902,337 filed the Nov. 11, 2013, hereby incorporated by reference in its entirety.

ACKNOWLEDGEMENT

This invention was made with government support under Grant No. MH085617 awarded by the National Institutes of Health. The government has certain rights in the invention.

BACKGROUND

Many neurological diseases are characterized by an imbalance of neuronal excitability, leading to disturbed neuronal connectivity and, in some cases, convulsive seizures. Examples of neurological diseases with deficiencies in the regulation of neuronal excitability are epilepsy, autism, spectrum disorders (ASDs), fragile X syndrome (FXS), and Alzheimer's disease (AD). Levisohn reports that there is a connection between autism and epilepsy. Epilepsia. 2007, 48 Suppl 9:33-5. Noebels reports that epilepsy and Alzheimer's dementia intersect in the hippocampal formation. Epilepsia. 2011, 52 Suppl 1:39-46.

The voltage-gated potassium channel Kv4.2 contributes to inwardly rectifying potassium currents (a.k.a. A-type currents) in the hippocampus. Kv4.2-mediated A-currents are important for action potential shaping and regulate dendritic excitability by limiting the back-propagation of action potentials. Kv4.2 plays important role in processing and transmitting information. Kv4.2 mRNA and protein levels are regulated by neuronal activity, and several different brain disorders are characterized by aberrant Kv4.2 expression. Singh et al. report Kv4.2 truncation mutation in a patient with temporal lobe epilepsy. Neurobiol Dis (2006) 24, 245-253. Gross et al. report Fragile X mental retardation protein regulates protein expression and mRNA translation of the potassium channel Kv4.2. J Neurosci (2011) 31, 5693-5698. Lee et al. report bidirectional regulation of dendritic voltage-gated potassium channels by the fragile X mental retardation protein, Neuron (2011) 72, 630-642. Hall et al. report Tau and potassium channel Kv4.2 in Alzheimer disease-related neuronal dysfunction, (2011) Neuroscience Meeting Planner. Washington, D.C.: Society for Neuroscience, 2011. Online.

MicroRNAs (miR), originally identified in plants, are typically 21-23 nucleotides in length and arise from longer precursors which are transcribed from non-protein-encoding genes. The precursors form structures that fold back on each other in self-complementary regions and are then processed by the nuclease Dicer in animals or DCL1 in plants. MicroRNA molecules interrupt translation through precise or imprecise base-pairing with their targets and are involved in gene regulation. Some miRNAs inhibit protein synthesis by binding to partially complementary 3' untranslated regions (UTRs) of target mRNAs. Others function like siRNA and bind to perfectly complementary mRNA sequences to destroy the target transcript.

Matkovich et al., report microRNA-133a protects against myocardial fibrosis and modulates electrical repolarization without affecting hypertrophy in pressure-overloaded adult hearts. Circ Res (2010) 106, 166-175. Kim et al. report microRNAs that co-purify with polyribosomes in mammalian neurons. Proc Natl Acad Sci USA. 2004, 101(1):360-5.

Jimenez-Mateos et al. report silencing microRNA-134 produces neuroprotective and prolonged seizure-suppressive effects. Nat Med, 2012, 18(7):1087-94. See also Jimenez-Mateos & Henshall, Neuroscience, 2013, 238:218-29.

References cited herein are not an admission of prior art.

SUMMARY

This disclosure relates to manipulating microRNA for the management of neurological disorders and compositions related thereto. In certain embodiments, the disclosure contemplates inhibition of miR324 or miR324-5p, e.g., the use of nucleobase polymers for antisense disruptions or RNA interference of miR-324 expression or miR324-5p binding in order to increase Kv4.2 expression as a therapeutic strategy.

In certain embodiments, the disclosure relates to methods of treating or preventing a neurological disease or condition comprising administering to a subject in need thereof an effective amount of a nucleobase polymer, wherein the nucleobase polymer comprises a sequence selected from a) a miR-324 sequence or fragment, b) a sequence configured to hybridize to a miR-324 sequence, and c) a sequence configured to hybridize to a Kv4.2 target sequence of miR-324-5p. In certain embodiments, the neurological disease is fragile X syndrome, autism spectrum disorders, epilepsy, dementia, and Alzheimer's disease.

In certain embodiments, the miR-324 sequence is a sequence selected from: hsa-pri-miR-324 CUGACUAUGC-CUCCCCGCAUCCCCUAGGGCAU UGGU-GUAAAGCUGGAGACCC ACUGCCCCAG-GUGCUGCUGGGGGUUGUAGUC (SEQ ID NO:1); mature hsa-miR-324-5p CGCAUCCCCUAGGGCAUUG-GUGU (SEQ ID NO: 2); mature hsa-miR-324-3p ACUGC-CCAGGUGCUGCUGG (SEQ ID NO: 3); or pre-miR-324 stem loop sequence AAAGCUGGAG (SEQ ID NO: 4).

In certain embodiments, the sequence configured to hybridize to a miR-324 sequence comprises CACCAATGC-CCTAGGGGATG (SEQ ID NO: 5) or TGC-CCTAGGGGATGC (SEQ ID NO: 6).

In certain embodiments, the Kv4.2 target sequence is GCACUGCAGUGUUUCUCAUG GGGAUGCA (SEQ ID NO:7).

In certain embodiments, the sequence configured to hybridize to a Kv4.2 target sequence of miR-324-5p comprises GTGTGCATCCCCATGAGAA (SEQ ID NO: 8).

In certain embodiments, the nucleobase polymer has a sequence of more than 7, 8, 9, 10, 11, 12, 13, 14, 15 or more nucleotides or nucleobases or continuous nucleotide nucleobases that is the reverse complement of SEQ ID NO: 1, 2, 3, 4, or 7. In certain embodiments, the nucleobase polymer is less than 100, 50, or 25 nucleobases or base pairs. In certain embodiments, the nucleobase polymer is more than three nucleotides but less than seven, or more than four nucleotides but less than seven, or more than five nucleotides but less than seven.

In certain embodiments, the nucleobase polymer comprises monomers of (LNA) 1-(hydroxymethyl)-2,5-dioxabicyclo[2.2.1]heptan-7-ol, ribose, deoxyribose, 2'-O-methy ribose, 2'-0-methoxyethyl ribose, 2'-fluororibose, phosphodiester, phosphorothioate, methylphosphonate, phosphorodiamidate, piperazine phosphorodiamidate, P-(2-(hydroxymethyl)morpholino)-N,N-dimethylphosphonamidate, morpholin-2-ylmethanol, (2-(hydroxymethyl)morpholino) (piperazin-1-yl)phosphinate, or peptide nucleic acids or combinations thereof.

In certain embodiments, pharmaceutical composition comprising a pharmaceutically acceptable excipient and a nucleobase polymer disclosed herein. In certain embodiments, the nucleobase polymer comprises SEQ ID NO: 1, 2, 3, 4, 5, 6, 7, 8, or fragment or reverse complement thereof. In certain embodiments, the nucleobase polymer is double or single stranded. In certain embodiments, the fragment is greater than 5, 10, 15, or 20 nucleotides or nucleobases. In certain embodiments, the fragment is less than 100, 50, or 25 nucleotides or nucleobases or base pairs.

In certain embodiments, the disclosure relates to synthetic, non-naturally occurring nucleobase polymer comprising a sequence described herein or variants thereof. In certain embodiments, the variant has 98%, 95%, 90%, 85%, 80%, 75%, 70%, 65%, 60%, or 50% sequence identity thereto.

In certain embodiments, the disclosure relates to synthetic, non-naturally occurring nucleobase polymers comprising or consisting of a sequence configured to hybridize to a Kv4.2 target sequence of miR-324-5p, e.g., GTGTG-CATCCCCATGAGAA (SEQ ID NO: 8).

In certain embodiments, the disclosure relates to compositions, e.g., pharmaceutical compositions, and uses reported herein comprising synthetic, non-naturally occurring nucleobase polymer comprising TGCCCTAGGGGATGC (SEQ ID NO: 6), AATGCCCTAGGG (SEQ ID NO: 9), or ACCAATGCCCTAGGGGA (SEQ ID NO: 18), with monomers of 1-(hydroxymethyl)-2,5-dioxabicyclo[2.2.1]heptan-7-ol and one or more phosphorothioate linkages.

BRIEF DESCRIPTION OF THE FIGURES

FIG. 2A shows data indicating MiR-324-5p represses recombinant and endogenous Kv4.2 protein expression. MiR-324-5p target region on Kv4.2 mouse and rat 3'UTRs, seed region is shown in green. Two nucleotides differ in the mouse and rat 3'UTRs (highlighted in yellow), but do not affect miR-324-5p targeting. Luciferase constructs were based on the rat sequence.

FIG. 2B shows experimental data where Neuro2a cells were transfected with Kv4.2 firefly luciferase 3'UTR reporters and pre-microRNA expressing plasmids.

FIG. 2C shows experimental data of antagomirs.

FIG. 2D shows experimental data where mutating two nucleotides in the seed region of the Kv4.2 3'UTR (shown on top, mutated nucleotides in red) abolishes the inhibitory effect of miR-324-5p overexpression).

FIG. 2E shows experimental data indicating increases in luciferase activity compared to the wild type reporter. Luciferase activity was normalized to co-transfected *Renilla* firefly, scrambled microRNA sequences served as negative control.

FIG. 2F shows data on MiR-324-5p inhibition.

FIG. 2G shows data on overexpression using pre-microRNA expressing lentiviral particles.

FIG. 2H shows data on increases or reduces endogenous Kv4.2 protein expression in cultured cortical neurons.

FIG. 2I shows data indicating overexpression of pre-miR-324-5p reduces Kv4.2 cell surface expression. Surface expression was measured using surface biotinylation following lentiviral expression of pre-miR-324-5p in cultured cortical neurons FIG. 1H.

FIG. 2J shows data using quantitative immunofluorescence under non-permeabilizing conditions in transfected cultured hippocampal neurons. Neurons in were identified by expression of a GFP reporter on the pre-miRNA plasmid. Scale bar is 25 µm.

FIG. 3A shows data indicating inhibition of miR-324-5p prevents kainic acid-induced neurotoxicity and Kv4.2 down-regulation and reduces seizure activity. Propidium iodide staining in live neurons transfected with scrambled or miR-324-5p antagomirs 4 hours following treatment with 10 µM kainic acid. DAPI staining was used as a counter-stain.

FIG. 3B shows the percentage of propidiumiodide-positive cells normalized to scrambled control (Kruskal-Wallis test p=0.036; Dunn's posthoc tests *p=0.0364; n.s.p>0.9999).

FIG. 3C shows data indicating antagonizing miR-324-5p prevents kainic acid-induced reduction of Kv4.2 protein levels (also see FIG. 1H) (paired t-tests; scrambled: *p=0.0105; anti-miR324-5p: p=0.3244). Antagomirs were expressed for less than 24 hours, and increased Kv4.2 protein levels in the untreated samples was not detected, which probably also is the reason for lack of effect on cell survival under control levels.

DETAILED DISCUSSION

Figure 1A:
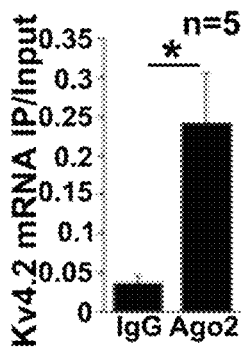
FIG. 1A shows data indicating Kv4.2 mRNA is regulated by the RISC during status epilepticus. Kv4.2-specific qRT-PCRs of mRNA isolated from Ago2-IPs using hippocampal tissue.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the term "combination with" when used to describe administration with an additional treatment means that the agent may be administered prior to, together with, or after the additional treatment, or a combination thereof.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the condition or disease is eradicated. Rather, embodiments, of the present disclosure also contemplate treatment that merely reduces symptoms, and/or delays conditions or disease progression.

As used herein, the term "nucleic acid" is intended to mean a ribonucleic or deoxyribonucleic acid or analog thereof, including a nucleic acid analyte presented in any context; for example, a probe, target or primer. A nucleic acid can include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which base-pairs with cytosine, adenine or uracil. Alternatively or additionally, oligonucleotides, nucleotides or nucleosides including the above-described non-native bases can further include reversible blocking groups on the 2', 3' or 4' hydroxyl of the sugar moiety.

The terms "binding," "binds," "recognition," or "recognize" as used herein are meant to include interactions between molecules that may be detected using, for example, a hybridization assay. When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). Any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

Sequence "identity" refers to the number of matching nucleotides (expressed as a percentage) in a sequence alignment between two sequences of the alignment window. As used herein, percentage identity of an alignment is calculated using the number of identical positions divided by the greater of the shortest sequence or the number of equivalent positions excluding overhangs wherein internal gaps are counted as an equivalent position. For example the nucleotide CCCCCC and CCCCCT have a sequence identity of 4 out of 5 or 80%. For example, the polypeptides CCCTTT and CCCATTT have a sequence identity of 6 out of 7 or 85%.

The Use of microRNAs to Modulate Kv4.2 Function as a Therapy for Neurological Conditions A gene for fragile X mental retardation protein is Fmr1. In Fmr1 knock-out mice, Kv4.2 protein levels and Kv4.2 cell surface levels are reduced in brain slices and cultured neurons. See Gross et al., (2011) Fragile X mental retardation protein regulates protein expression and mRNA translation of the potassium channel Kv4.2, J Neurosci 31, 5693-5698. This indicates that aberrant Kv4.2 expression contributes to the epileptic phenotype and hyper-excitability observed in Fmr1 KO mice. Thus, increasing Kv4.2 expression levels in Fmr1 KO is believed to rescue neuronal dysfunction in FXS. It is believed that Kv4.2 dysfunction contributes to neuronal hyperexcitability and to cognitive defects in fragile X syndrome.

Data herein indicates that a specific microRNA, miR-324-5p, negatively regulates the expression of the voltage-gated potassium channel Kv4.2, the major regulator of dendritic excitability in the hippocampus. Kv4.2 is dysregulated in several neurological diseases, such as fragile X syndrome, other autism spectrum disorders, epilepsy and Alzheimer's disease. It is believed that manipulating miR-324-5p and/or other microRNAs targeting Kv4.2 can be used as a therapeutic strategy to correct dysregulated Kv4.2 expression and function underlying altered neuronal excitability.

Kv4.2 mediates transient inactivating somatodendritic A-type currents (IA) in the hippocampus, which regulate the back-propagation of action potentials, and are thus important for synaptic signal integration and control of neuronal excitability. Deletion of Kv4.2 increases seizure susceptibility in mice, and truncation or gain-of-function mutations in Kv4.2 have been associated with epilepsy in human patients, suggesting an important role of Kv4.2 in the etiology of epilepsy. In line with this hypothesis, Kv4.2 expression and function are modulated in animal models of temporal lobe epilepsy. In particular, protein levels are altered after kainic acid- or pilocarpine-induced seizures, but the molecular mechanisms regulating Kv4.2 expression during neuronal hyperactivity are unknown.

Inhibiting miR-324-5p increases Kv4.2 expression (or blocks it's decrease during excitotoxic events) and thus decreases neuronal excitability. This is useful in several diseases with an imbalance of excitatory and inhibitory network activity in the brain, e.g., Fragile X (direct link to Kv4.2 by us: Gross, Yao, Bassell et al., 2011; Journal of Neuroscience, and Lee, Yan et al., 2011, Neuron), Alzheimer's and epilepsy.

Experiments herein indicate a role for RNA-induced silencing and miR-324-5p in regulating Kv4.2 protein expression during excitotoxic events. This corroborates findings that Kv4.2 is subject to tight translational control. Moreover, these results add to evidence that microRNA-induced silencing is a mechanism underlying epilepsy, and suggest that RNA-induced silencing of Kv4.2 by miR-324-5p is a viable strategy to therapeutically target, in particular, by inhibition of miR-324-5p or other related approaches that result in increased Kv4.2 expression.

In certain embodiments, the disclosure contemplates treating a subject at risk of, diagnosed with, or exhibiting symptoms of a neurological disorder, e.g., seizures or epilepsy, by administering a nucleobase polymer disclosed herein, optionally in combination with an anti-convulsive agent, e.g., lamotrigine, levetiracetam, phenytoin, carbamazepine, ethotoin, phenobarbital, ethosuximide, trimethadione, and valproate. Other examples of neurological disorders include subjects having, at risk of, suspected of having, or diagnosed with benign rolandic epilepsy, childhood absence epilepsy, and juvenile myoclonic epilepsy, febrile seizures, and benign neonatal seizures. In certain embodiments, the subject may experience at least two unprovoked (or reflex) seizures occurring greater than 24 hours apart.

Epilepsy is a neurological disorder characterized by seizures. Seizures episodes can vary. A subject is typically diagnosed with epilepsy when they experience recurring seizures that are not the result of immediate injury or induced by medication, e.g., drugs, alcohol. In many instances, the cause of seizures is unknown. Subject may develop epilepsy as the result of brain injury, stroke, brain cancer, and drug and alcohol misuse. Epilepsy is typically confirmed with an electroencephalogram (EEG). In certain embodiments, subjects may experience seizures that are convulsive or non-convulsive, tonic-clonic, tonic, clonic, myoclonic, absence, atonic, with or without the loss of consciousness.

Fragile X syndrome (FXS), is a genetic syndrome that typically causes intellectual disabilities ranging from mild to severe as well as physical characteristics such as an elongated face, large or protruding ears, and large testes (macroorchidism), and behavioral characteristics such as stereotypic movements (e.g. hand-flapping), and social anxiety. Fragile X syndrome relates to the expansion of the CGG trinucleotide repeat in the Fragile X mental retardation 1 (FMR1) gene on the X chromosome. The fragile X mental retardation protein (FMRP) is required for normal neural development. It is often the genetic cause of autism. The fragile X abnormality is typically diagnosed by analysis of the number of CGG repeats on the X chromosome.

In certain embodiments, the disclosure contemplate treating an subject at risk of, diagnosed with, or exhibiting symptoms of a neurological disorder, e.g., FXS, by administering a nucleobase polymer disclosed herein optionally in combination with antidepressants, selective serotonin reuptake inhibitors (SSRIs), antipsychotics, risperidone, quetiapine, anticonvulsants, mGluR5 antagonists, mavoglurant, dipragluran, lithium, neuropeptide oxytocin (OT), or combinations thereof.

In certain embodiments, the disclosure contemplated the treatment of autism spectrum disorders with nucleobase polymers disclosed herein. Autism Spectrum Disorder, including Asperger Syndrome, is a spectrum of neurodevelopmental disorders characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities.

In certain embodiments, the disclosure contemplate treating or prevent an subject at risk of, diagnosed with, or exhibiting symptoms of Alzheimer's disease by administering an effective amount of a nucleobase polymer disclosed herein. The disease is associated with plaques and tangles in the brain. Sporadic AD is typical, and many subjects possess at least one APOEε4 allele which is a risk factor. AD can be attributed to mutations in several other genes such as amyloid precursor protein (APP) and presenilins 1 and 2. Mutations in the APP and presenilin genes increase the production of Aβ42 the main component of senile plaques.

In certain embodiments, the disclosure contemplate treating or prevent an subject at risk of, diagnosed with, or exhibiting symptoms of Alzheimer's disease by administering an effective amount of a nucleobase polymer disclosed herein in combination with acetylcholinesterase inhibitors, tacrine, rivastigmine, galantamine, donepezil, antipsychotic, memantine, huperzine A, or combinations thereof.

Nucleobase Polymers and miR-324

It is believed that microRNAs are initially transcribed as part of one arm of an about 80 nucleotide RNA stem-loop (termed a primary microRNA or pri-miRNA). Each pri-miRNA may contain several microRNA precursors that potentially undergo processing and cleavage by proteins and enzymes to form precursor microRNAs (pre-miRNAs). Pre-miRNAs are then exported out of the nucleus and into the cytoplasm where the pre-miRNA hairpin is cleaved by an RNase enzyme (Dicer). Dicer is thought to interact with the 3' end of the hairpin and cuts away the loop joining the 3' and 5' arms resulting in an unstable microRNA duplex, and ultimately resulting in a mature miR-3p and miR-5p.

The microRNA database (http://www.mirbase.org/) reports miR-324. miR-324-5p originates from the 5p end of the miRNA stem loop (pre-miRNA) and miR-324-3p originates from the 3p end. Certain examples disclosed herein utilize probes to mi-R324-5p; however, the methods and compositions disclosed herein may be utilized with nucleobase polymers or nucleobase polymers that hybridize to miR-324-5p, miR-324-3p, pre-miR-324, or pri-miR-324.

The sequence of human pri-miR-324 is CUGACUAUGCCUCCCCGCAUCCCCUAGGGCAUUGGU-GUAAAGCUGGAGACCCACU GCCCCAG-GUGCUGCUGGGGGUUGUAGUC (SEQ ID NO: 1).

The sequence of miR-324-5p in humans is (SEQ ID NO: 2) CGCAUCCCCUAGGGCAUUGGUGU.

The sequence of miR-324-3p in humans is (SEQ ID NO: 3) ACUGCCCCAGGUGCUGCUGG.

Human pre-miR-324 stem-loop structure contains the following loop sequence (SEQ ID NO: 4) AAAGCUGGAG.

The term "nucleobase polymer that hybridizes" refers to a molecule capable of hybridizing to a single-stranded nucleic acid target. The nucleobase polymer may target, e.g., comprise a sequence that is the reverse complement of, more than 7, 8, 9, 10, 11, 12, 13, 14, 15, 20, or more nucleotides or nucleobases or continuous nucleotide nucleobases of SEQ ID NO: 1, 2, 3 or 4. The nucleobase polymer may be single stranded nucleic acid or analog containing a sufficiently small number of mismatches, additions, or deletions as long as the probe retains the ability to bind to the target. The nucleobase polymer may be the single stranded tail of a double stranded nucleic acid. The nucleobase polymer may be a part of a loop structure or single stranded tail of a hairpin structure. In certain embodiments, the nucleobase polymer may be less than 500, 200, 100, 50, or 25 nucleotides or nucleobases.

In certain embodiments, the nucleobase polymer contains the reverse complement of SEQ ID NO: 2. Examples include AATGCCCTAGGG (SEQ ID NO: 9), TAGGGGATGCG (SEQ ID NO: 10), ACACCAATGCC (SEQ ID NO: 11).

In certain embodiments, the nucleobase polymer contains the reverse complement of SEQ ID NO: 3. Examples include: AGCACCTGG (SEQ ID NO: 12), TGGGGCAGT (SEQ ID NO: 13) and CCAGCAGCA (SEQ ID NO: 14)

In certain embodiments, the nucleobase polymer contains the reverse complement of SEQ ID NO: 4. Examples include CAGCTTT (SEQ ID NO: 15), CCAGCT (SEQ ID NO: 16), and CTCCAG (SEQ ID NO: 17).

In certain embodiments, the disclosure contemplates the use of nucleobase polymers for antisense disruptions of miR-324 or RNA interference of miR-324 expression to increase Kv4.2 expression. RNA interference (RNAi) enables sequence specific gene silencing by promoting degradation of specific mRNAs. In certain embodiments, it is contemplated that the nucleobase polymer is an antisense to SEQ ID NO: 1-4 or 7. In certain embodiments, it is contemplated that the nucleobase polymer is a short double-stranded nucleobase polymers, e.g., double stranded RNA molecules (siRNA), comprising fragments of SEQ ID NO: 1-4.

The term "nucleobase polymer" refers to a polymer comprising nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleic acid may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding. With regard to the nucleobases, it is contemplated that the term encompasses isobases, otherwise known as modified bases, e.g., are isoelectronic or have other substitutes configured to mimic naturally occurring hydrogen bonding base-pairs, e.g., within any of the sequences herein U may be substituted for T, or T may be substituted for U. Examples of nucleotides with modified adenosine or guanosine include, but are not limited to, hypoxanthine, xanthine, 7-methylguanine Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. Nos. 6,001,983; 6,037,120; 6,617, 106; and 6,977,161). In another embodiment, a removable base (such as uracil or 8-oxoguanine) is contemplated so that treatment by uracil-DNA glycosylase (UDG) or formamidopyrimidine-DNA glycosylase (FPG), can lead to cleavage and degradation of unwanted sequences.

In order to prevent in vivo breakdown nucleic acids may be chemically modified, e.g., within the sugar backbone or on the 5' or 3' ends. As such, in certain embodiments, nucleobase polymers disclosed herein may contain monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-yl-methanol, (2-(hydroxymethyl)morpholino) (piperazin-1-yl) phosphinate, or peptide nucleic acids or combinations thereof.

Within any of the sequences disclosed herein, U may be T or T may be U. In certain embodiments, the fragment is greater than 5, 10, 15, or 20 nucleotides or nucleobases but less than 100, 50, or 25.

In certain embodiments, the nucleotide base polymer is single or double stranded RNA that is 3' end capped with one, two, or more thymidine nucleotides and/or the passenger strand of the RNA comprises 5' end polyphosphate, e.g., di-phosphate, tri-phosphate.

In certain embodiments, the disclosure relates to compounds, compositions, and methods disclosed herein using nucleobase polymers. In particular, the instant disclosure features nucleic acid molecules, such as antisense nucleobase polymers, short interfering short interfering RNA (siRNA), double-stranded RNA (dsRNA), micro-RNA (miRNA), short hairpin RNA (shRNA) molecules, and chemically modified forms thereof.

RNA interference initially discovered in plants as Post-Transcriptional Gene Silencing (PTGS), is a highly conserved mechanism triggered by double-stranded RNA (dsRNA) and able to down regulate transcript of genes homologous to the dsRNA. The dsRNA is first processed by Dicer into short duplexes of 21-23 nucleotides, called short interfering RNAs (siRNAs). Incorporated in RNA-induced silencing complex (RISC), they are able to mediate gene silencing through cleavage of the target mRNA. "siRNA" or "small-interfering ribonucleic acid" refers to two strands of ribonucleotides which hybridize along a complementary region under physiological conditions. The siRNA molecules comprise a double-stranded region which is substantially identical to a region of the mRNA of the target, e.g., SEQ ID NO: 1-4. A region with 100% identity to the corresponding sequence of the target is an example. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art.

The length of the region of the siRNA complementary to the SEQ ID NO: 1-4, in accordance with the present disclosure, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer.

Pharmaceutical Compositions

In certain embodiments, the disclosure relates to pharmaceutical compositions comprising a nucleotide base polymer disclosed herein, e.g., comprising a miR-324 sequence or hybridizes to a miR-324 sequence, or the target of miR-324 on Kv4.2 and a pharmaceutically acceptable excipient.

In certain embodiments, the disclosure relates to pharmaceutical compositions comprising a double or single stranded nucleotide base polymer comprising or consisting essentially of: (SEQ ID NO: 1, 2, 3, 4, 5, 6, 7, or 8) or fragments thereof wherein U may be T, optionally comprising isobases.

In certain embodiments, the pharmaceutical composition is in the form of a pill, capsule, tablet, gel, or aqueous buffer comprising a saccharide.

In certain embodiments, the pharmaceutical composition comprising a nucleobase polymer can comprise a delivery vehicle, including liposomes, for administration to a subject, carriers and diluents and their salts, and/or can be present in pharmaceutically acceptable formulations. U.S. Pat. Nos. 6,395,713 and 5,616,490 further describe general methods for delivery of nucleic acid molecules.

Formulating siRNA within polymeric or lipid nanoparticles (LNPs) is a strategy to prevent degradation. In certain embodiments, nucleobase polymers disclosed herein are containing in a particle comprising an ionizable lipid, a neutral helper lipid, cholesterol, and a diffusible polyethylene glycol (PEG)-lipid. See Semple et al., Nature Biotech, 2010, 28(2), 172-6. In another example, nucleobase polymers disclosed herein are containing in a particle comprising a cyclodextrin polymer. See Zuckerman et al., J Invest Dermatol, 2011, 131, 453-60.

Nucleobase polymers can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example U.S. Pat. Nos. 7,141,540 and 7,060,498), poly(lactic-co-glycolic)acid (PLGA) and PLCA microspheres (see for example U.S. Pat. No. 6,447,796), biodegradable nanocapsules, and bioadhesive microspheres, or by proteinaceous vectors (U.S. Pat. No. 7,067,632). In another embodiment, the nucleobase polymers can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In one embodiment, a nucleobase polymer is complexed with membrane disruptive agents such as those described in U.S. Pat. No. 6,835,393. In another embodiment, the membrane disruptive agent or agents and nucleobase polymers are also complexed with a cationic lipid or helper lipid molecule, such as those lipids described in U.S. Pat. No. 6,235,310.

Embodiments of the disclosure feature a pharmaceutical composition comprising one or more nucleobase polymers in an acceptable carrier, such as a stabilizer, buffer, and the like. The nucleobase polymers or oligonucleotides can be administered and introduced into a subject by any standard means, with or without stabilizers, buffers, and the like, to form a pharmaceutical composition. When it is desired to use a liposome delivery mechanism, standard protocols for formation of liposomes can be followed. The compositions can also be formulated and used as tablets, capsules or elixirs for oral administration, suppositories for rectal administration, sterile solutions, suspensions for administration by injection, and the other compositions known in the art.

Embodiments of the disclosure also feature the use of the composition comprising surface-modified liposomes containing poly (ethylene glycol) lipids (PEG-modified, or long-circulating liposomes or stealth liposomes). These formulations offer a method for increasing the circulation and accumulation of in target tissues. The long-circulating liposomes enhance the pharmacokinetics and pharmacodynamics of DNA and RNA. See U.S. Pat. Nos. 5,820,873 and 5,753,613. Long-circulating liposomes are also likely to protect from nuclease degradation.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques.

In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

The compositions will generally be administered in an "effective amount", by which is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 100 mg of nucleobase polymer per kilogram body weight of the patient per day, more often between 0.01 and 50 mg, such as between 0.1 and 2.5 mg, for example about 0.1, 0.5, 1, 5, 10, 2, 5, 10, 15, 20 or 25 mg of nucleobase polymer, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated.

Synthesis of Nucleobases Polymers

A "synthetic, non-naturally occurring nucleobase polymer" is a nucleobase polymer created by human intervention through chemical synthesis or expression through the use of a recombinant vector and typically amplification, e.g., PCR. The synthetic, non-naturally occurring nucleobase polymer is typically less than about one hundred nucleotides or less than fifty nucleotides.

One may chemically synthesize oligonucleotides (e.g., certain modified oligonucleotides or portions of oligonucleotides) using protocols known in the art as, for example, described in U.S. Pat. No. 6,001,311. The synthesis of oligonucleotides makes use of common nucleic acid protecting and coupling groups, such as dimethoxytrityl at the 5'-end and phosphoramidites at the 3'-end. In a non-limiting example, small scale syntheses are conducted on a 394 Applied Biosystems, Inc. synthesizer using a 0.2 micro mol scale protocol with a 2.5 min coupling step for 2'-O-methylated nucleotides and a 45 second coupling step for 2'-deoxy nucleotides or 2'-deoxy-2'-fluoro nucleotides. Alternatively, syntheses at the 0.2 micro mol scale can be performed on a 96-well plate synthesizer, such as the instrument produced by Protogene (Palo Alto, Calif.) with minimal modification to the cycle. A 33-fold excess of 2'-O-methyl phosphoramidite and a 105-fold excess of S-ethyl tetrazole can be used in each coupling cycle of 2'-O-methyl residues relative to polymer-bound 5'-hydroxyl. A 22-fold excess of deoxy phosphoramidite and a 70-fold excess of S-ethyl tetrazole mop can be used in each coupling cycle of deoxy residues relative to polymer-bound 5'-hydroxyl. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PerSeptive Biosystems, Inc.). S-Ethyltetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

Deprotection of the DNA-based oligonucleotides is performed as follows: the polymer-bound trityl-on oligonucleotide is transferred to a 4 mL glass screw top vial and suspended in a solution of 40% aqueous methylamine (1 mL) at 65 degrees for 10 minutes. After cooling to −20 degrees, the supernatant is removed from the polymer support. The support is washed three times with 1.0 mL of EtOH:MeCN:$H_2O$/3:1:1, vortexed and the supernatant is then added to the first supernatant. The combined supernatants, containing the oligonucleotide, are dried.

Alternatively, the nucleic acid molecules can be synthesized separately and joined together post-synthetically, for example, by ligation or by hybridization following synthesis and/or deprotection.

Nucleic acids can also be assembled from two distinct nucleic acid strands or fragments wherein one fragment includes the sense region and the second fragment includes the antisense region of the RNA molecule.

The nucleic acid molecules can be modified extensively to enhance stability by modification with nuclease resistant groups, for example, 2'-amino, 2'-O-allyl, 2'-fluoro, 2'-O-methyl, 2'-H). Constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See e.g., U.S. Pat. Nos. 5,652,094, 5,334,711, and 6,300,074. All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

In one embodiment, nucleic acid molecules include one or more (e.g., about 1, 2, 3, 4, 5, 6, 7, 8, 9, 10, or more) G-clamp nucleotides. A G-clamp is a tricyclic aminoethyl-phenoxazine 2'-deoxycytidine or analogue. See Lin &. Matteucci, J Am Chem Soc, 1998, 120, 8531-8532; Flanagan, et al., Proc Nat Acad Sci USA, 1999, 96, 3513-3518; and Maier, et al., Biochemistry, 2002, 41, 1323-1327. A single G-clamp analog substitution within an oligonucleotide can result in substantially enhanced helical thermal stability and mismatch discrimination when hybridized to complementary oligonucleotides. The inclusion of such nucleotides in nucleic acid molecules results in both enhanced affinity and specificity to nucleic acid targets, complementary sequences, or template strands.

In another embodiment, nucleic acid molecules include one or more (e.g., about 1, 2, 3, 4, 5, 6, 7, 8, 9, 10, or more) LNA "locked nucleic acid" nucleotides e.g. backbone monomers of 1-(hydroxymethyl)-2,5-dioxabicyclo[2.2.1]heptan-7-ol, (see for example U.S. Pat. Nos. 6,639,059, 6,670,461, 7,053,207).

In another embodiment, the disclosure features conjugates and/or complexes of nucleobase polymers. Such conjugates and/or complexes can be used to facilitate delivery of polymers into a biological system, such as a cell. Contemplated conjugates include those with cell penetrating peptide. The conjugates and complexes provided may impart therapeutic activity by transferring therapeutic compounds across cellular membranes, altering the pharmacokinetics, and/or modulating the localization of nucleic acid molecules. In general, the transporters described are designed to be used either individually or as part of a multi-component system, with or without degradable linkers. These compounds are expected to improve delivery and/or localization of nucleic acid molecules into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

In another aspect a nucleobase polymers comprises one or more 5' and/or a 3'-cap structure, for example on only the sense strand, the antisense strand, or both strands.

A "cap structure" refers to chemical modifications, which have been incorporated at either terminus of the oligonucleotide. See, for example, Adamic et al., U.S. Pat. No. 5,998, 203. These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925).

In one embodiment, the disclosure features modified nucleobase polymer, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions.

RNAi Gene Therapy

RNA interference (RNAi) enables sequence specific gene silencing by promoting degradation of specific mRNAs with short double-stranded RNA molecules (siRNA). In certain embodiments, the disclosure contemplates methods of treating neurological diseases or conditions comprising an RNAi gene therapy, e.g., administering a viral vector configured to express nucleic acids that interfere or interrupt miR-324 expression, to a subject in need thereof. In certain embodiments, the viral vector expresses a 18 to 25, or 20 to 22 nucleotide double stranded nucleotide comprising SEQ ID NO: 1, 2, 3, 4, 5, 6, 7, or 8 or fragment thereof for RNA interference of the expression of miR324.

As used herein, the term "gene therapy" refers to a method of delivering DNA or RNA molecules to a target cell. This delivery may be accomplished by either viral vectors or by non-viral vectors with viral vectors being the typical choice. The purpose of gene therapy may be to modulate, induce, or inhibit gene expression. This may be accomplished by using the vector to deliver DNA or RNA to the target cell and thereby express proteins or protein components capable of affecting gene expression in the target cell. This may also be accomplished by using RNA molecules capable of regulating gene expression at the transcriptional or post-transcriptional level. Induction of gene expression may be accomplished by the insertion of a functional gene (the transgene) into a target cell. Herein, this disclosure focuses on miR324 with neuron cells being the typical target cell type.

Recombinant viral vectors include, but are not limited to, recombinant adeno-associated virus (rAAV), recombinant retrovirus, recombinant adenovirus, recombinant poxvirus, and recombinant herpes simplex virus (HSV). The choice of recombinant viral vector used depends on the type of genetic material (e.g. RNA or DNA, single-stranded or double-stranded) to be transferred to the target cell. Several types of retrovirus are available including, but not limited to, lentivirus and gamma-retrovirus (e.g. murine leukemia virus), with lentivirus being the typical choice. A retrovirus may be used to transfer RNA, which is subsequently incorporated randomly into the target cell's genome by the enzymes reverse transcriptase and integrase. Multiple serotypes of rAAV (e.g. AAV1, AAV2, and other AAV serotypes) may be used. rAAV may be used to transfer single-stranded DNA. Recombinant adenovirus does not incorporate into a target cell's genome, but rather expresses free DNA in the nucleus and may be considered transient. Recombinant adenovirus may be used to transfer double-stranded DNA. Poxvirus is used to transfer double-stranded DNA. HSV is typically used to target neurons as it is capable of latently infecting those cells. HSV may be used to transfer double-stranded DNA. Of the viral vector methods of gene therapy, rAAV-mediated gene delivery is the typical choice. rAAV is considered non-immunogenic, i.e. an individual will not typically mount an immune response to clear it, and it is capable of infecting non-dividing, quiescent cells.

RNA molecules may be used to interfere with gene expression. Small hairpin RNA (shRNA), also known as short hairpin RNA, may be introduced into a target cell and may be constitutively expressed by the H1 or U6 promoters. The shRNA is capable of inhibiting target gene expression by RNA interference. shRNA is cleaved, forming small interfering RNA (siRNA). siRNAs are double-stranded. The RNA-induced silencing complex binds to the siRNA, and the siRNA in turn binds to a target mRNA sequence which is then cleaved. This may be used to disrupt mRNA translation. Antisense RNA may also be used to modulate mRNA translation. Antisense RNA is single-stranded RNA that binds to complementary mRNA thereby obstructing its ability to translate. Furthermore, oligonucleotide "decoys" may be used to bind transcription factors, thereby reducing transcription factor binding for the target gene.

Non-viral vectors may also be used for gene therapy. As disclosed herein, non-viral vectors of gene therapy for the treatment or prevention of neurological diseases or conditions include, but are not limited to, plasmid DNA, polymer-DNA complexes, matrix-DNA complexes, and liposome-DNA complexes. Non-viral gene therapy may be augmented through the use of techniques capable of enhancing entry into the target cell including, but not limited to, electroporation, enveloping the DNA with a liposomal or polymer coating, magnetofection, sonoporation, and particle bombardment with a "gene gun." Typically, these augmentation methods are used in vitro.

Gene therapy is currently a well-characterized, established methodology with both viral and non-viral delivery well-known in the art for the treatment of a variety of conditions including, but not limited to, cardiovascular disease, pain reduction, limb ischemia, alpha-1-antitrypsin deficiency, and cancer. See, e.g., Jessup et al. Circulation. 2011, 124(3):304-313, Anghel, et al. Curr Neurovasc Res. 2011, Flotte et al. Hum Gene Ther. 2011, Shirakawa, T., et al. Hum Gene Ther. 2007, 18(12):1225-32, US Published Patent Application Nos. US 2003/0082137 A1, US 2004/0029227 A1, and US 2006/0063732 A1.

One ordinarily skilled in the art will be capable of creating and administering a recombinant viral vector for the purpose of gene therapy. A recombinant viral vector may be created by a process comprising isolating the transgene of interest, incorporating it into a recombinant viral expression vector (the construct), and administering the construct to the target in order to incorporate the transgene. Numerous recombinant viral expression vectors are commercially available for these purposes. The exact protocol for generating a recombinant viral vector may vary depending on the choice of the viral vector. Example protocols for generating rAAV, the typical choice of viral vector, as well as recombinant retrovirus are disclosed in Heilbronn et al., Viral vectors for gene transfer: current status of gene therapeutics. Handb Exp Pharmacol. 2010, (197):143-70.

EXAMPLES

Antagomirs

Antagomirs studied were locked-nucleic acid-modified as reported herein. Antagomirs also typically differ from normal RNA by the following modifications: 2'-O-methylation of sugar, one or more or all phosphorothioate linkages, and a cholesterol moiety at 3' end. For in vitro assays, has-miR-324-5p miRCURY LNA™ microRNA inhibitor sequence ACCAATGCCCTAGGGGA (SEQ ID NO: 18), or scrambled "Negative control A" or "Negative control B" TAACACGTCTATACGCCCA (SEQ ID NO: 19) or AGAGCTCCCTTCAATCCAA (SEQ ID NO: 20), were used (obtained from Exiqon). miRCURY LNA™ microRNA is miRNA wherein 5'-phosphates are removed from the microRNA termini using Calf Intestinal Alkaline Phosphatase (CIP) and a fluorescent label is enzymatically attached to the 3'-end of the microRNAs. For in vivo applications, a custom-made in vivo inhibitor (LNA 15nt) for miR-324-5p, with a partial phosphorothioate backbone and no cholesterol tag specific, and a scrambled control with the same features were used (prepared by Exiqon). Lentiviral pre-microRNA-expressing plasmids were obtained from GeneCopoeia. Lentiviral particles expressing pre-microRNAs were generated by the Emory University Viral Vector Core using these plasmids. The following qRT-PCR primers were used:

```
                                      (SEQ ID NO: 21)
Kv4.2 for: GTTCTATGGTTGGGCTGTG;

(SEQ ID NO: 22)
Kv4.2 rev: GTGGCTCTAACTGTATCTATG;

(SEQ ID NO: 23)
β-Actin for: GGGGTGTTGAAGGTCTCAAA;

(SEQ ID NO: 24)
β-Actin rev: ACTGGGACGACATGGAGAAG;

(SEQ ID NO: 25)
miR-324-5p: CGCATCCCCTAGGGCATTGGTGT;
```

LNA-modified miR-324-5p and miR-330-specific probes for FISH were obtained from Exiqon and labeled with digoxigenin by 3'-end tailing (Roche Applied Life Sciences). For Kv4.2 luciferase reporters, Kv4.2 3'UTR was PCR-amplified from rat cDNA and subcloned into pGL3-Promoter Vector (Promega) at the 3' end of the firefly luciferase cDNA. Point mutations were introduced by PCR using specific primers.

Figure 1B:
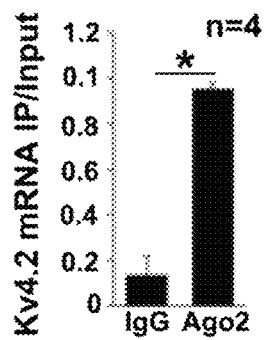
FIG. 1B shows data on Kv4.2-specific qRT-PCRs of mRNA isolated from Ago2-IPs using cultured hippocampal neurons.
Figure 1C:
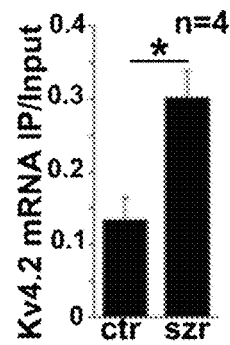
FIG. 1C show data on significant enrichment of Kv4.2 mRNA compared to IgG. Kv4.2 mRNA association with Ago2 is increased 30 min after onset of kainic acid-induced status epilepticus).
Figure 1D:
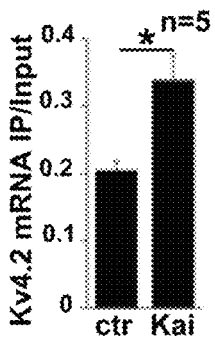
FIG. 1D shows data 4 hours following neurotoxicity-inducing kainic acid treatment in neurons (10 µM kainic acid, paired t-test, *p=0.034).
Figure 1E:
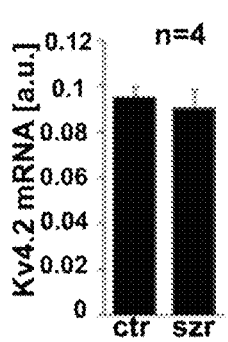
FIG. 1E shows data on seizures or excitotoxicity did not affect Kv4.2 mRNA levels, but led to significantly reduced Kv4.2 protein levels.
Figure 1F:
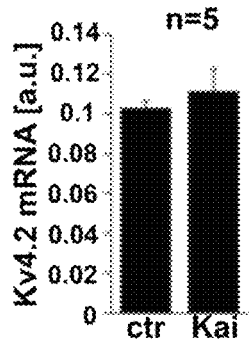
FIG. 1F shows experimental data.
Figure 1G:
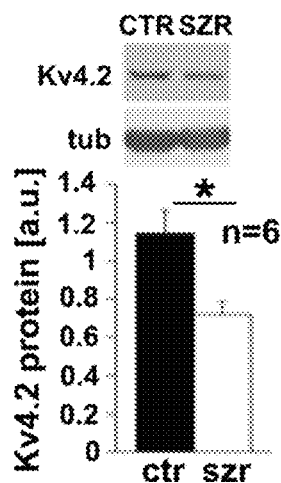
FIG. 1G shows experimental data.

The Potassium Channel Kv4.2 is Regulated by RNA-Induced Silencing During Epileptic Seizures To investigate whether RNA-induced silencing regulates Kv4.2 expression in the brain during epileptic seizures, Kv4.2 mRNA was quantified in Ago2-specific immunoprecipitates (IPs) from brain tissue. Ago2 is a prominent component of the RNA-induced silencing complex (RISC) that associates with mRNAs prone to microRNA-mediated silencing. Using quantitative real-time PCR, specific enrichment of Kv4.2 mRNA was detected in Ago2-IPs from hippocampal lysates (FIG. 1A) and cultured hippocampal mouse neurons (FIG. 1B). To analyze if the RISC may be involved in the regulation of Kv4.2 expression during epileptic seizures, the association of Kv4.2 mRNA with Ago2 was quantified 30 min following kainic acid-induced seizure onset in living mice, as well as 4 hours following excitotoxicity-inducing treatment with kainic acid in hippocampal neurons. Both in vivo and in vitro, neuronal hyperexcitation led to increased association of Kv4.2 mRNA with Ago2 (FIGS. 1C and 1D), whereas total Kv4.2 mRNA levels were unchanged (FIGS. 1E, and 1F). Both treatments led to reduced Kv4.2 protein levels (FIGS. 1G and 1H), suggesting that translational suppression of Kv4.2 mRNA by the RISC may contribute to the downregulation of Kv4.2 protein following status epilepticus.

Bioinformatic analyses (miRBase, Targetscan) identified miR-324-5p as a putative candidate with a matching seed region (FIG. 2A). To assess if miR-324-5p regulates Kv4.2 expression, a luciferase reporter construct was generated containing the Kv4.2-3'UTR. Luciferase assays in Neuro2A (N2A) cells co-expressing the reporter construct and pre-miR-324-5p (FIG. 2B) or a locked-nucleic acid (LNA)-modified antagomir containing the miR-324-5p antisense sequence (FIG. 2C) showed that miR-324-5p negatively regulates Kv4.2 expression. A reporter construct bearing a double point mutation in the seed region-targeting sequence of the Kv4.2 3'UTR was not affected by overexpression of pre-miR-324-5p (FIG. 2D), and had increased basal luciferase activity compared to the wild type sequence, most likely because of lack of inhibition by endogenous miR-324-5p (FIG. 2E). Together, these results corroborate the specific regulation of Kv4.2 mRNA by miR-324-5p.

Whether miR-324-5p controls endogenous Kv4.2 protein levels in neurons was examined Inhibition of miR-324-5p in cortical neurons using LNA-antisense probes significantly increased endogenous Kv4.2 protein levels (FIG. 2F). In contrast, total Kv4.2 mRNA levels were not affected, suggesting that miR-324-5p leads to translational suppression, but not degradation of Kv4.2 mRNA. Vice versa, viral overexpression of pre-miR-324-5p significantly reduced Kv4.2 protein in cortical neurons (FIG. 2G). Kv4.2 executes its role as a potassium channel on the cell membrane. To assess the functional relevance of miR-324-5p regulation of Kv4.2, the effect of miR-324-5p overexpression was quantified on Kv4.2 cell surface expression. Using surface biotinylation in cortical neurons, as well as non-permeabilizing fluorescence immunocytochemistry in hippocampal neurons, significantly reduced Kv4.2 surface expression was detected following miR-324-5p overexpression (FIGS. 2H, 2I, and 2J).

Figure 1H:
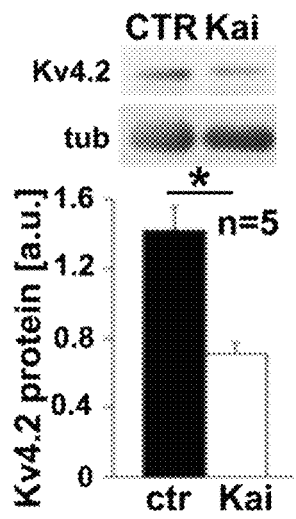
FIG. 1H shows experimental data.
Figure 3D:
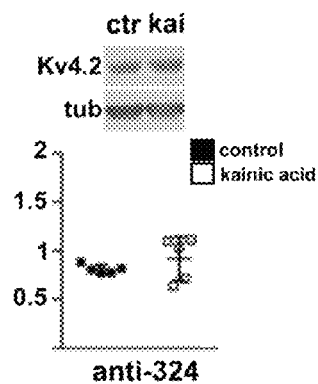
FIG. 3D shows data indicating intracerebroventricular injections of miR-324-5p antagomirs increased time until seizure onset following intra-amygdala kainic acid injection.

Downregulation or deletion of Kv4.2 leads to increased excitability of neurons, which can be fatal, as in the case of epilepsy. Experiments herein indicate that miR-324-5p-induced silencing of Kv4.2 may exacerbate neuronal excitation and neurotoxicity during events that can lead to epilepsy. Thus, blocking miR-324-5p may protect neurons from excitotoxicity and epileptic activity. To test this hypothesis, kainic acid-induced cell death was quantified in cultured neurons transfected with miR-324-5p-specific antagomirs. Increased cell death was detected after 4 hrs incubation with 10 µM kainic acid in hippocampal neurons transfected with scrambled antagomirs (FIGS. 3A and 3B), and Kv4.2 protein expression was significantly decreased under these conditions (FIG. 3C, also see FIG. 1H). In contrast, kainic acid treatment did not lead to increased cell death or reduced Kv4.2 protein levels in neurons that were transfected with miR-324-5p-specific antagomirs (FIGS. 3B and 3D). These results indicate a neuroprotective function of antagonizing miR-324-5p, which is at least partially mediated by preventing RNA-induced silencing of Kv4.2.

Figure 3E:
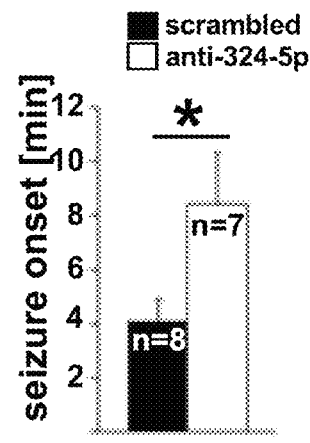
FIG. 3E shows experimental data.
Figure 3F:
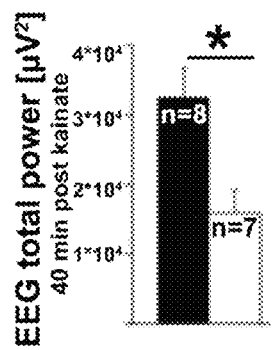
FIG. 3F shows data indicating intracerebroventricular injections of miR-324-5p antagomirs reduced total EEG power.
Figure 3G:
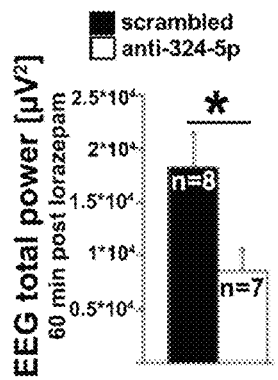
FIG. 3G shows data indicating intracerebroventricular injections of miR-324-5p antagomirs reduced total EEG power.
Figure 3H:
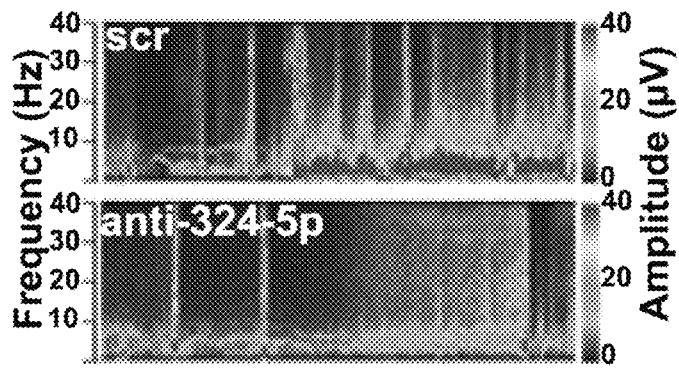
FIG. 3H shows data indicating antagonizing miR-324-5p reduces seizure-induced cell death in the ventral hippocampus as shown by Fluoro-Jade B staining (independent t-test, *p=0.025).
Figure 3I:
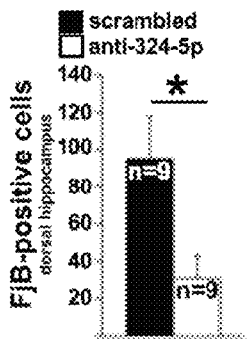
FIG. 3I shows data on western blot analyses from hippocampal tissue of mice injected with vehicle, scrambled control or anti-miR-324-5p in different doses as indicated (0.1 and 0.5 nmol). 0.5 nmol antagomir showed robust reduction of miR-324-5p, significantly increased Kv4.2 expression (independent t-test, *p=0.025).
Figure 3J:
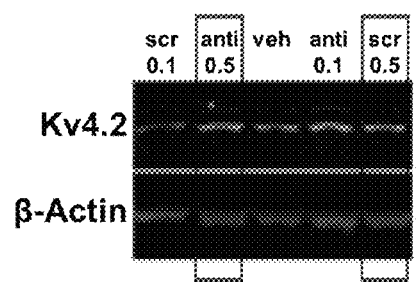
FIG. 3J shows experimental data.
Figure 3K:
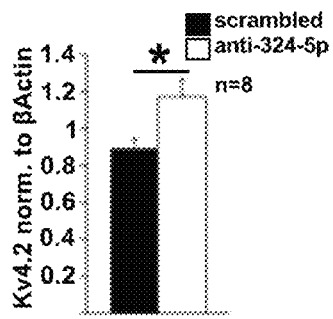
FIG. 3K shows experimental data.

Changes in total hippocampal miR-324-5p levels were not detect 30 min following kainic acid-induced seizure. In contrast miR-324-5p association with Ago2 was increased, similarly as observed for Kv4.2 mRNA (FIGS. 3C and 3D). This suggested an acute role of miR-324-5p during epileptic seizures. To test this hypothesis, whether intracerebroventricular injection of miR-324-5p-specific antagomirs protects against kainic acid-induced cell death and seizure susceptibility in live mice was analyzed. Mice were injected with antagomirs or scrambled controls 24 hours before induction of status epilepticus by intra-amygdala injection of kainic acid Antagonizing miR-324-5p before induction of status epilepticus significantly increased the time until seizure onset (FIG. 3E) and reduced the total EEG power compared to scrambled control (FIGS. 3,F and 3G), suggesting that antagonizing miR-324-5p suppresses seizures. In addition, Fluoro-Jade B staining showed a neuroprotective effect of anti-miR-324-5p in the hippocampus, resulting in less neuronal death following kainic acid-induced seizure (FIG. 3I). Western blot analyses of hippocampal tissue showed significantly increased expression of Kv4.2 in mice injected with miR-324-5p-specific antagomirs (FIGS. 3J and 3K), again suggesting that at least part of miR-324-5p's anti-convulsant and neuroprotective activity is through blocking microRNA-mediated silencing of Kv4.2.

Intracerebroventricular Injection of microRNAs and Seizure Models

For intarcerbroventricular injections of miR-324-5p-specific or scrambled antagomirs, mice received a cannula ipsilateral to the side of kainic acid injection at bregma: AP=−0.3 mm, L=−1.0 mm, ventral (V)=−2.0 mm. Mice received a 5 µl infusion of either scrambled or miR-324-5p specific antagomirs in aCSF. Mice were either euthanized to quantify miR-324-5p or Kv4.2 protein, or received kainic acid injections into the basolateral amygdala nucleus as described below to induce status epilepticus 24 hours later.

For experiments shown in FIGS. 1A to 1H, seizures were induced in male mice between postnatal days 24 and 28 by intraperitoneal injection of kainic acid (15 mg/kg). Mice were monitored throughout the entire experiment and euthanized 30 min after the onset of status epilepticus. Status epilepticus was defined as a full tonic-clonic seizure. Hippocampal tissue was dissected on ice and immediately used for experiments. Experiments shown in FIGS. 3A to 3K were done using a mouse-adapted stereotaxic frame. Four partial craniectomies were done on anesthesized mice to place skull-mounted recording screws (Bilaney Consultants) and a guide cannula (coordinates from the bregma: anterior-posterior (AP)=−0.94 mm, lateral (L)=−2.85 mm). EEG was recorded using a Grass Comet digital EEG on freely moving mice. See Jimenez-Mateos et al. Nat Med (2012). Nat Med., 2012, 18(7):1087-94. After establishing baseline EEG, kainic acid or vehicle (PBS) were injected into the basolateral amygdala nucleus while lightly restraining mice. After 40 min, mice received lorazepam (Ativan, 6 mg per kg body weight, intraperitoneally). Mice were recorded for up to 1 h, disconnected and transferred to a recovery chamber.

LNA™-Anti-miR-324-5p Inhibition of Kv4.2

Incubation of Neuro 2a cells with LNA™-anti-miR-324-5p (3 days) (T*G*C*C*C*T*A*G*G*G*G*A*T*G*C) (SEQ ID NO: 6 wherein *=phosphorothioate) significantly increases the activity of a Kv4.2-3'UTR luciferase reporter construct compared to a scrambled control LNA™ probe (n=4, *p<0.05, t-test). In primary cortical neurons, incubation of LNA™-antimiR-324-5p (3 days) leads to increased endogenous Kv4.2 protein levels as analyzed by western blotting. Example western blot is shown on the bottom, Kv4.2-specific signal was normalized to β-tubulin-specific signal on the same blot (n=2). Error bars represent SEM.

Figure 4A:
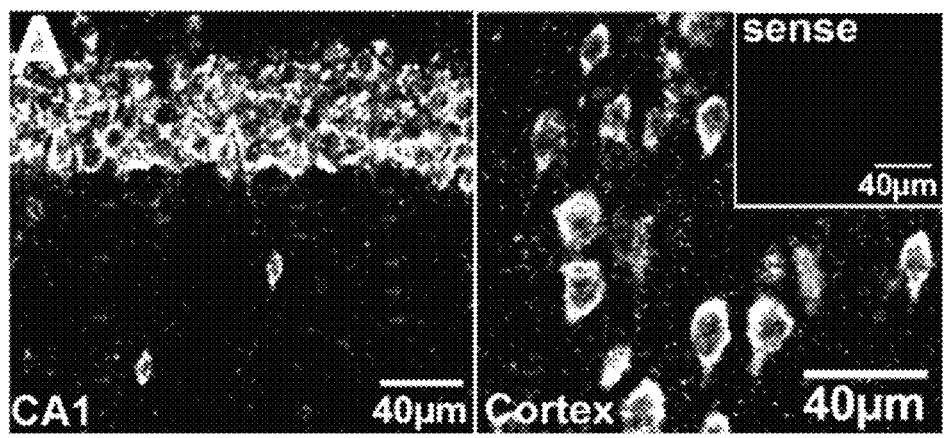
FIG. 4A shows data indicating miR-324-5p-mediated regulation of Kv4.2 mRNA translation can occur locally in dendrites. Kv4.2 mRNA and miR-324-5p are expressed in the same regions in hippocampal neurons. A Quantitative FISH using a Kv4.2 specific riboprobe shows that Kv4.2 mRNA can be detected in somata and dendrites in the mouse CA1 area and cortex. A sense probe does not result in detectable signal.
Figure 4B:
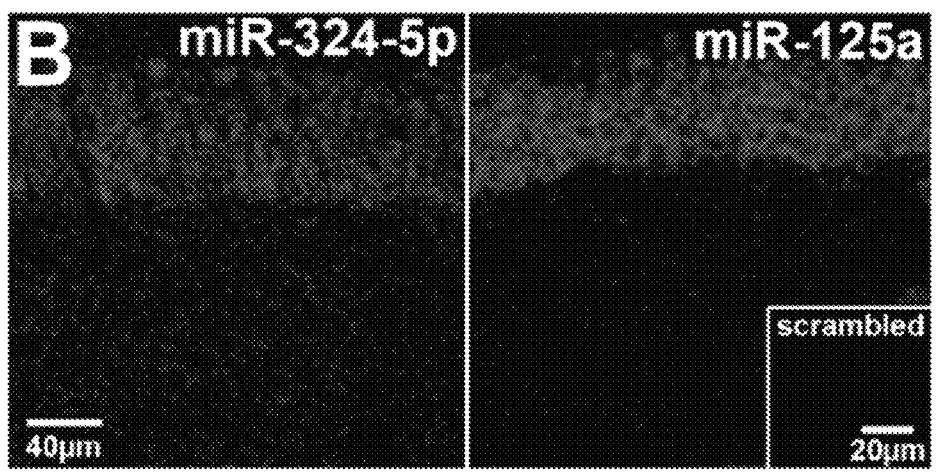
FIG. 4B shows data on FISH using LNA-modified oligonucleotides shows that miR-324-5p is expressed in the mouse CA1 area.
Figure 4C:
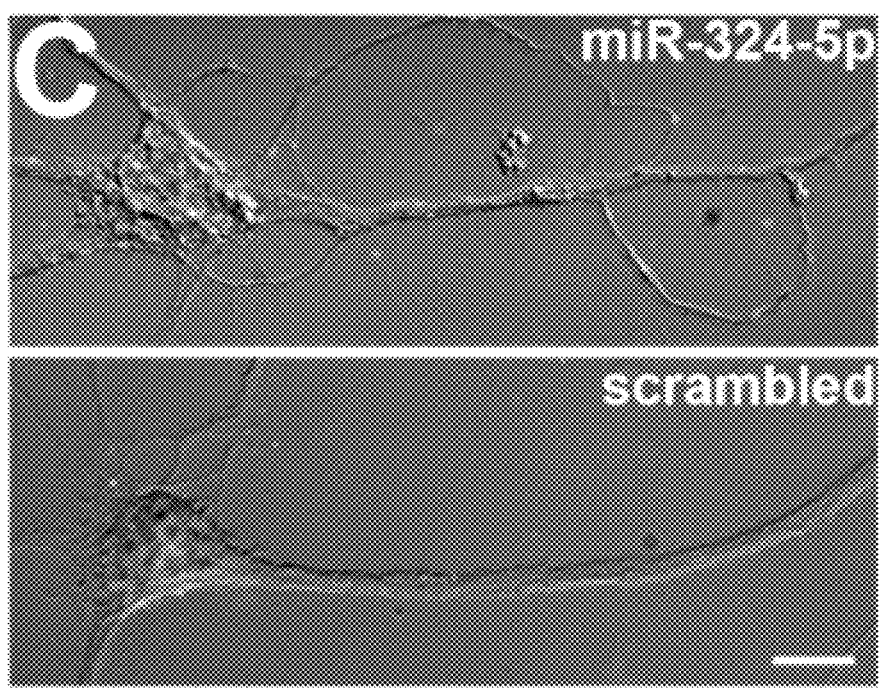
FIG. 4C shows data in cultured hippocampal neurons. The expression pattern in the CA1 area is the same as miR-125a, a dendritic microRNA. Scrambled probes show no specific signal.

Kv4.2 mRNA and miR-324-5p are expressed in the same regions in hippocampal neurons. A Quantitative FISH using a Kv4.2 specific riboprobe shows that Kv4.2 mRNA can be detected in somata and dendrites in the mouse CA1 area and cortex. FIG. 4 A, a sense probe does not result in detectable signal. B,C FISH using LNA-modified oligonucleotides shows that miR-324-5p is expressed in the mouse CA1 area (FIG. 4B) and in cultured hippocampal neurons (FIG. 4C). The expression pattern in the CA1 area is the same as miR-125a, a dendritic microRNA. Scrambled probes show no specific signal.

Kv4.2 Target Site Inhibition

In certain embodiments, the disclosure contemplates a therapeutic using a "target site inhibitor" which masks the miR-324-5p binding site on the Kv4.2 mRNA. This option is more specific to Kv4.2, because microRNAs usually have many targets, which would probably be affected by inhibiting miR-324-5p as well. One example is (G*T*G*T*G*C*A*T*C*C*C*C*A*T*G*A*G*A*A) (*=phosphorothioate).

In certain embodiments, the disclosure relates to a therapeutic product comprising a target site inhibitor nucleobase polymer which hybridizes the miR-324-5p binding site on the Kv4.2 mRNA, GCACUGCAGUGUUUCU-CAUGGGGAUGCA (SEQ ID NO: 7). In one embodiment, the nucleobase polymer specific for the target site on Kv4.2, has the following sequence G*T*G*T*G*C*A*T*C*C*C*C*A*T*G*A*G*A*A (SEQ ID NO: 8) wherein * is phosphorothioate Alternative Approaches In certain embodiments, the disclosure relates to a therapeutic product comprising a sequence complementary to the seed region in the stem loop sequence of the miR-324.

Staton & Giraldez report the use of target protector morpholinos to analyze the physiological roles of specific miRNA-mRNA pairs in vivo. See Nature protocols, 2011, 6(12):2035. In certain embodiments, the disclosure contemplates nucleobase polymers disclosed herein comprising substituted morpholine monomers.

An alternate approach, rather than impeding processing, aims to bind all mature miRNAs. By stably overexpressing an mRNA in a vector with multiple miRNA-binding sites, polymer with monomers of the reverse-complement of a miRNA-324, e.g., miRNA-324-5p, or fragment thereof disclosed herein, the miRNA binds this ectopic transcript rather than its endogenous target. They are used to soak up the mature miRNA, i.e., miRNA sponges.

The invention claimed is:

1. A method of treating fragile X syndrome comprising administering to a subject in need thereof an effective amount of a nucleobase polymer, wherein the nucleobase polymer comprises a sequence selected from CACCAATGCCCTAGGGGATG (SEQ ID NO: 5) or TGCCCTAGGGGATGC (SEQ ID NO: 6) and wherein T may be substituted for U.

2. The method of Claim 1, wherein the nucleobase polymer is less than 100 or 50 nucleobases.

3. The method of claim 1, wherein the nucleobase polymer comprises monomers of (LNA) 1-(hydroxymethyl)-2,5-dioxabicyclo[2.2.1]heptan-7-ol, ribose, deoxyribose, 2'-O-methy ribose, 2-O-methoxyethyl ribose, 2'-fluororibose, phosphodiester, phosphorothioate, methylphosphonate, phosphorodiamidate, piperazine phosphorodiamidate, P-(2-(hydroxymethyl)morpholino)-N,N-dimethylphosphonamidate, morpholin-2-ylmethanol, (2-(hydroxymethyl) morpholino) (piperazin-1-yl)phosphinate, or peptide nucleic acids or combinations thereof.

* * * * *

SEQUENCE LISTING

<160> NUMBER OF SEQ ID NOS: 25

<210> SEQ ID NO 1
<211> LENGTH: 83
<212> TYPE: DNA
<213> ORGANISM: Artificial Sequence
<220> FEATURE:

<223> OTHER INFORMATION: Synthetic construct

<400> SEQUENCE: 1
cugacuaugc cucccgcau ccccuagggc auugguguaa agcuggagac ccacugcccc    60
aggugcugcu ggggguugua guc    83

<210> SEQ ID NO 2
<211> LENGTH: 23
<212> TYPE: DNA
<213> ORGANISM: Artificial Sequence
<220> FEATURE:
<223> OTHER INFORMATION: Synthetic construct

<400> SEQUENCE: 2
cgcauccccu agggcauugg ugu    23

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
acugccccag gugcugcugg    20

<210> SEQ ID NO 4
<211> LENGTH: 10
<212> TYPE: DNA
<213> ORGANISM: Artificial Sequence
<220> FEATURE:
<223> OTHER INFORMATION: Synthetic construct

<400> SEQUENCE: 4
aaagcuggag    10

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
caccaatgcc ctaggggatg    20

<210> SEQ ID NO 6
<211> LENGTH: 15
<212> TYPE: DNA
<213> ORGANISM: Artificial Sequence
<220> FEATURE:
<223> OTHER INFORMATION: Synthetic construct

<400> SEQUENCE: 6
tgccctaggg gatgc    15

<210> SEQ ID NO 7
<211> LENGTH: 28
<212> TYPE: DNA
<213> ORGANISM: Artificial Sequence
<220> FEATURE:
<223> OTHER INFORMATION: Synthetic construct

<400> SEQUENCE: 7
gcacugcagu guuucucaug gggaugca    28

```
<210> SEQ ID NO 8
<211> LENGTH: 19
<212> TYPE: DNA
<213> ORGANISM: Artificial Sequence
<220> FEATURE:
<223> OTHER INFORMATION: Synthetic construct

<400> SEQUENCE: 8
gtgtgcatcc ccatgagaa                                                    19

<210> SEQ ID NO 9
<211> LENGTH: 12
<212> TYPE: DNA
<213> ORGANISM: Artificial Sequence
<220> FEATURE:
<223> OTHER INFORMATION: Synthetic construct

<400> SEQUENCE: 9
aatgccctag gg                                                           12

<210> SEQ ID NO 10
<211> LENGTH: 17
<212> TYPE: DNA
<213> ORGANISM: Artificial Sequence
<220> FEATURE:
<223> OTHER INFORMATION: Synthetic construct

<400> SEQUENCE: 10
accaatgccc tagggga                                                      17

<210> SEQ ID NO 11
<211> LENGTH: 11
<212> TYPE: DNA
<213> ORGANISM: Artificial Sequence
<220> FEATURE:
<223> OTHER INFORMATION: Synthetic construct

<400> SEQUENCE: 11 tagggatgc g                                                             11

<210> SEQ ID NO 12
<211> LENGTH: 11
<212> TYPE: DNA
<213> ORGANISM: Artificial Sequence
<220> FEATURE:
<223> OTHER INFORMATION: Synthetic construct

<400> SEQUENCE: 12
acaccaatgc c                                                            11

<210> SEQ ID NO 13

<400> SEQUENCE: 13

000

<210> SEQ ID NO 14

<400> SEQUENCE: 14

000

<210> SEQ ID NO 15

<400> SEQUENCE: 15
```

000

<210> SEQ ID NO 16
<400> SEQUENCE: 16

000

<210> SEQ ID NO 17
<400> SEQUENCE: 17

000

<210> SEQ ID NO 18
<400> SEQUENCE: 18

000

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
taacacgtct atacgccca                                          19

<210> SEQ ID NO 20
<211> LENGTH: 19
<212> TYPE: DNA
<213> ORGANISM: Artificial Sequence
<220> FEATURE:
<223> OTHER INFORMATION: Synthetic construct

<400> SEQUENCE: 20
agagctccct tcaatccaa                                          19

<210> SEQ ID NO 21
<211> LENGTH: 19
<212> TYPE: DNA
<213> ORGANISM: Artificial Sequence
<220> FEATURE:
<223> OTHER INFORMATION: Synthetic construct

<400> SEQUENCE: 21
gttctatggt tgggctgtg                                          19

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
gtggctctaa ctgtatctat g                                       21

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

```
<400> SEQUENCE: 23
ggggtgttga aggtctcaaa                                              20

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
ctgggacgac atggagaag                                               19

<210> SEQ ID NO 25
<211> LENGTH: 23
<212> TYPE: DNA
<213> ORGANISM: Artificial Sequence
<220> FEATURE:
<223> OTHER INFORMATION: Synthetic construct

<400> SEQUENCE: 25
cgcatcccct agggcattgg tgt                                          23
```